(12) United States Patent
Brown et al.

(10) Patent No.: US 7,961,843 B2
(45) Date of Patent: Jun. 14, 2011

(54) RADIOTHERAPEUTIC APPARATUS

(75) Inventors: Kevin Brown, Horsham (GB); Ralph Streamer, Horsham (GB); Paul Boxall, Crawley (GB); Duncan Bourne, Redhill (GB)

(73) Assignee: Elekta AB (publ), Stockholm (SE)

( * ) Notice: Subject to any disclaimer, the term of this patent is extended or adjusted under 35 U.S.C. 154(b) by 99 days.

(21) Appl. No.: 12/297,891

(22) PCT Filed: Apr. 27, 2006

(86) PCT No.: PCT/EP2006/003901
§ 371 (c)(1),
(2), (4) Date: Feb. 10, 2009

(87) PCT Pub. No.: WO2007/124760
PCT Pub. Date: Nov. 8, 2007

(65) Prior Publication Data
US 2009/0213991 A1    Aug. 27, 2009

(51) Int. Cl.
*A61N 5/10* (2006.01)

(52) U.S. Cl. ........................................................ 378/65
(58) Field of Classification Search .................... 378/65
See application file for complete search history.

(56) References Cited

U.S. PATENT DOCUMENTS

| | | | | |
|---|---|---|---|---|
| 5,663,999 | A * | 9/1997 | Siochi | 378/65 |
| 5,818,902 | A * | 10/1998 | Yu | 378/65 |
| 6,038,284 | A * | 3/2000 | Hernandez-Guerra et al. | 378/65 |
| 6,052,430 | A * | 4/2000 | Siochi et al. | 378/65 |
| 6,052,435 | A * | 4/2000 | Hernandez-Guerra et al. | 378/150 |
| 6,108,399 | A * | 8/2000 | Hernandez-Guerra et al. | 378/65 |
| 6,134,296 | A * | 10/2000 | Siochi | 378/65 |
| 6,240,161 | B1 * | 5/2001 | Siochi | 378/65 |
| 6,249,565 | B1 * | 6/2001 | Tarr | 378/65 |
| 6,314,159 | B1 * | 11/2001 | Siochi | 378/65 |
| 6,330,300 | B1 * | 12/2001 | Siochi | 378/65 |

(Continued)

FOREIGN PATENT DOCUMENTS

EP    0586152 A    3/1994

OTHER PUBLICATIONS

Duthoy, W., et al., "Clinical Implementation of Intensity-Modulated Arc Therapy (IMAT) for Rectal Cancer" International Journal of Radiation: Oncology Biology Physics, Pergamon Press, U.S., vol. 60, No. 3, Nov. 1, 2004, pp. 794-806. PCT International Search Report, Aug. 12, 2006.

*Primary Examiner* — Allen C. Ho
(74) *Attorney, Agent, or Firm* — Z. Peter Sawicki; Westman, Champlin & Kelly, P.A.

(57) ABSTRACT

A radiotherapeutic apparatus comprises a source able to emit a beam of therapeutic radiation along a beam axis, a multi-leaf collimator arranged to collimate the beam to a desired shape, wherein the source is rotatable about a rotation axis that is substantially orthogonal and intersects with the beam axis thereby to describe an arc around that axis, and further comprises a control means able to control the dose/time rate of the source, the rotation speed of the source, and the multi-leaf collimator position. The control means is arranged to control the source in accordance with a treatment plan over first and second arc-segments such that at least the multi-leaf collimator changes shape at a different rate per degree in the second arc-segment as to the first arc-segment.

14 Claims, 3 Drawing Sheets

U.S. PATENT DOCUMENTS

| | | | |
|---|---|---|---|
| 6,477,229 B1 * | 11/2002 | Grosser | 378/65 |
| 6,687,330 B2 * | 2/2004 | Hernandez-Guerra | 378/65 |
| 6,757,355 B1 * | 6/2004 | Siochi | 378/65 |
| 7,162,008 B2 * | 1/2007 | Earl et al. | 378/65 |
| 7,609,810 B2 * | 10/2009 | Yi et al. | 378/65 |
| 7,839,974 B2 * | 11/2010 | Shepard et al. | 378/65 |
| 7,880,154 B2 * | 2/2011 | Otto | 250/505.1 |

* cited by examiner

Fig 3 mu per degree

Fig 4 mu per degree

Fig 5

RADIOTHERAPEUTIC APPARATUS

CROSS-REFERENCE TO RELATED APPLICATION

This Application is a Section 371 National Stage Application of International Application No. PCT/EP2006/003901, filed Apr. 27, 2006 and published as WO 2007/124760 A1 on Nov. 8, 2007, the content of which is hereby incorporated by reference in its entirety.

FIELD OF THE INVENTION

The present invention relates to radiotherapeutic apparatus.

BACKGROUND ART

A radiotherapeutic apparatus is typically controlled by a Treatment Control Computer. When equipped with an Multi-Leaf Collimator ("MLC") the Treatment Control Computer can be considered to contain a Radiation Control Computer which controls the radiation generation, an MLC Control computer which controls the shape of the MLC and a Gantry Control Computer which controls the position of the Gantry. These computers may physically be one or more computers but in this text are considered as distinct functional elements of the system.

"Mu" is an abbreviation for "monitor units", which is the term used for units of radiation from the radiotherapeutic apparatus. An mu is equivalent to a unit of dose delivered to the patient under well defined calibration conditions. The relationship between mu and dose is modelled in the Treatment planning computer. The user interacts with the patient's prescription in units of dose but the Treatment planning computer defines the Treatment plan in units of mu. One of the tasks of a Treatment Planning computer is to ascertain the mu that need to be delivered by the apparatus in order to achieve a specific dose within the patient, both in terms of a sufficiently high dose in the tumour site and a sufficiently low dose in other parts of the patient. Informally, the use of the term 'dose rate' means 'mu rate'

Intensity Modulated Radiotherapy is a generic term for a number of radiotherapy techniques that, essentially, vary the beam that is directed at the patient. That variation can be spatial, temporal, or both.

Known linac delivery technologies include the following.

Segmental or Static Multi-Leaf Collimator—"SMLC"—is where the Multi-Leaf Collimator ("MLC") is static during irradiation. The MLC moves from one shape to the next in between irradiations. In one architecture, the point at which the irradiation stops and the MLC moves is controlled by the dosimetry hardware and Radiation Control computer. This results in exceptionally accurate delivery of dose per MLC shape. An alternative system uses a DMLC architecture to achieve the same effect. The MLC Control computer monitors the delivered dose and inhibits radiation when it detects it should move from one shape to the next. The inevitable control system delays associated with this architecture result in an uncertain dose per MLC shape and occasional missed shapes altogether.

Dynamic MLC—DMLC—is where the MLC moves during irradiation, with the gantry stationary. The MLC moves linearly from one shape to the next as a function of the delivered dose. The MLC control system has to monitor the delivered dose, and there is an inevitable delay. On older systems this delay was 200-300 ms, for more recent systems this is approximately 40 to 50 ms. This delay, together the response of the MLC, results in the shapes lagging behind the dose. This is extensively reported in the literature, but is widely regarded as not being clinically significant.

Rotational DMLC—RDMLC—is where the MLC moves during irradiation during a constant rotation of the gantry. The gantry moves at a constant mu per degree. The MLC moves linearly from one shape to the next as a function of the delivered dose. The shapes are usually, but not necessarily, defined at regular intervals around the arc. This can be achieved with a substantially independent MLC, Radiation and Gantry control computers.

Enhanced Rotational DMLC—ERDMLC—is where the MLC moves during irradiation during a rotation of the gantry and the gantry moves at a variable mu per degree. A variable gantry speed or variable dose rate (or both) can achieve the latter. Using variable dose rate alone has been analysed by the University of Gent as not being the preferred option as it gives longer delivery times. The MLC moves linearly from one shape to the next as a function of the delivered dose. The shapes and doses are usually, but not necessarily, defined at regular intervals around the arc. This technique requires a very high degree of integration between the MLC, Radiation and Gantry control computers and, to date, no linac has been able to deliver ERDMLC. At present, it is therefore a theoretical possibility only.

Treatment techniques involve a compatible treatment planning function and Linac delivery function, and known techniques are as follows:

Intensity Modulated Radiation Therapy—IMRT—is a sequence of MLC shapes with associated doses which can be delivered using SMLC and DMLC. The shapes are defined at a limited number of stationary gantry positions, typically 5 to 9. The shapes and doses are defined by an optimiser which attempts to meet objectives defined by the user. The treatment planning function is generally specific to the MLC constraints and the delivery technique.

Rotational Conformal Arc Treatments—RCAT—involves a constant rotation of the Gantry while the leaves are fitted dynamically to the projection of the target volume. This technique has been in use in Japan for many years. The delivery technique is RDMLC and only one arc is used.

Intensity Modulated Arc Therapy—IMAT—involves a treatment planning function in which the arcs and the positions of the leaves are not defined by the projection of the target volume but by an optimisation routine that tries to deliver the required dose distribution to the target and critical structures. In general a number of arcs are used over different ranges of gantry angles. The optimisation is like IMRT but includes the added flexibility of the rotational gantry. IMAT can be delivered via RDMLC, but this imposes a restriction on the optimisation of a constant mu per degree, which results in a sub-optimal plan. More ideally, the optimisation will be allowed complete freedom and an ERDMLC delivery technique will be used. The delivery times are exceptionally quick, typically 3 minutes for a complex plan. Superficially this technique looks the same as RCAT but the difference is how the MLC shapes are determined.

IMAT is discussed, for example, in Duthoy et al, "Clinical implementation of intensity-modulated arc therapy (IMAT) for rectal cancer", International Journal of Radiation Oncology, Volume 60, Issue 3, 1 Nov. 2004, pp 794-806 which ends "We identified significant potential for improvements both at the levels of planning and delivery. The single most important technical improvement for IMAT is the implementation of a variable gantry speed", i.e. an apparatus capable of ERDMLC.

Optimized Segment-Aperture Mono-Arc Therapy—OSA-MAT—is a special class of IMAT in which only one arc is used. This seems suitable for some clinical indications. It could also be regarded as a refinement of RCAT. Similar to IMAT the delivery technique can be simply RDMLC but more ideally ERDMLC. The delivery times are exceptionally quick, typically 1 minute.

Arc Modulation Optimisation Algorithm—AMOA—is the technique used by 3D Line Medical Systems. The leaf shapes are defined by the anatomy (as in RCAT) and then the arcs are divided into smaller sub arcs of about 20 degrees and the weight or mu per degree of these sub arcs are optimised to give the best dose distribution (similar to IMAT or IMRT). Thus, this is a form of IMAT or OSAMAT in which the option of modifying the leaf positions is not used. This is very quick to plan and to deliver, especially using the ERDMLC delivery technique.

Helical Intensity Modulated Arc Therapy—HIMAT—is a development of the IMAT technique where the patient is translated longitudinally simultaneously with the gantry rotation. This effectively makes the longitudinal length of the treatable field unlimited and truly competes with a Tomotherapy delivery solution. U.S. Pat. No. 5,818,902 and WO97/13552 show details of this. This typically has an MLC in a fixed orientation with the leaves moving across the patient. The MLC can have high-resolution leaves and a limited field size, as the field size can be extended by use of the helical technique.

The delivery technique for HIMAT can be simply RDMLC as the multiple rotations will allow the flexibility of increased dose from certain angles. The delivery times are exceptionally quick, typically 3 minutes for a complex plan.

SUMMARY OF THE INVENTION

It is possible that the ERDMLC delivery technique will give advantages, particularly to IMAT and HIMAT treatment plans. However, it has not proved possible to deliver ERDMLC in practice. A delivery technology that approximated to ERDMLC in terms of its capabilities but which was technically feasible to deliver would therefore be of great value.

Historically, all arcs have been delivered at a nominally constant rotation speed and constant dose rate, giving a fixed mu per degree of rotation. This requires constraints to be placed on the treatment planning optimisation which degrade the clinical quality of the plan. Further, there is a maximum speed at which the leaves of the multi-leaf collimator can move, and therefore at a given dose rate and dose for an arc segment there is a maximum distance they can travel. This is also a constraint in the planning, limiting the quality of the plan.

If the optimisation in the Treatment planning computer was to be allowed to vary the mu per degree, then it would put more dose into gantry angles that have fewer critical organs in the path of the radiation. For example, when treating the prostate, as the gantry rotates the bladder and rectum come in and out of the path of the radiation. It is not possible to avoid irradiating these organs completely, nor is it desirable (otherwise insufficient dose could be deposited into the prostate) but if the optimisation is allowed more flexibility in controlling the dose to these critical organs then it will be able to reduce the unwanted dose.

If the dose rate for the arc can be lowered, this will allow the planning more flexibility but increase the time for delivery, which is undesirable. An aim of this invention is to remove such constraints from the treatment planning process and therefore maximise the quality of the plan, while at the same time retaining a quick delivery time. Quick delivery times are important for departmental efficiency and (in high precision Image Guided Radiation Therapy) to prevent organ motion between imaging and the completion of irradiation.

According to the invention, a desired treatment is therefore described by the Treatment Planning computer in terms of a sequence of "control points". Each "control point" defines a position of the gantry, the dose that is to be delivered between this and the next (or previous) control point, and the shape of the MLC at that control point. Each consecutive pair of control points defines (between them) an arc-segment.

This treatment is put into effect by, between the $n^{th}$ and the $(n+1)^{th}$ control point, moving the gantry from the position of the $n^{th}$ control point to the position of the $(n+1)^{th}$ control point at a rotation speed and a dose rate that combine to deliver the required dose, while moving the MLC leaves so that when the gantry is at the $(n+1)^{th}$ control point, the leaves are in the correct position for that point. Typically, the MLC leaves will be moved at a rate which ensures that at all times their distance moved is linearly related to the dose that has been delivered in the arc-segment. This process is then repeated for the arc-segment between the $(n+1)^{th}$ and the $(n+2)^{th}$ control points, and so on until the treatment is complete.

Thus, we propose a radiotherapeutic apparatus comprising a source able to emit a beam of therapeutic radiation along a beam axis, a multi-leaf collimator arranged to collimate the beam to a desired shape, wherein the source is rotatable about a rotation axis that is substantially orthogonal to and intersects with the beam axis thereby to describe an arc around that axis, further comprising a control means able to control the dose/time rate of the source, the rotation speed of the source, and the multi-leaf collimator position, the control means being arranged to receive a treatment plan in which the arc is divided into a plurality of arc-segments, the treatment plan specifying the total dose for the arc-segment and a start and end MLC position, and to control the source in accordance with that plan over an first arc-segment such that at least one of the rotation speed and dose rate are constant and the multi-leaf collimator changes shape, and a second arc segment such that at least one of the rotation speed and dose rate are constant at a level different to the constant level adopted during the first arc-segment by calculating the total time required for the arc segment for a plurality of factors including an MLC leaf movement from a prescribed position at the start of the arc-segment to a prescribed position at the end of the arc-segment, at a maximum leaf speed, rotation of the source from the start to the end of the arc-segment at a maximum source rotation speed, delivery of the dose at a maximum dose rate per time, selecting the factor dictating the longest time, and controlling the apparatus so that the selected factor operates at its respective maximum and the remaining factors are operated at a reduced rate selected to match that longest time.

The control means will typically comprise a treatment control computer and an actuator.

The radiotherapeutic apparatus is preferably arranged to monitor the dose actually delivered during a treatment and the actual position of the source and/or MLC, compare this to the treatment plan, and servo the position of the source/MLC and or the dose rate so that the actual relationship between delivered dose and source position corresponds to the treatment plan.

Likewise, the radiotherapeutic apparatus is preferably arranged to monitor the dose actually delivered during a treatment and the actual position of the patient positioning system, compare this to the treatment plan, and servo the position of the patient positioning system and or the dose rate so that the actual relationship between delivered dose and patient positioning system position corresponds to the treatment plan.

The radiation is preferably not interrupted between the first arc-segment and the second arc-segment.

In this way, a system is produced that is sufficiently close to ERDMLC in practice to mean that it can be treated at an ERDMLC system for most purposes. This enables us to further propose a treatment planning apparatus for a radiotherapeutic apparatus of the type comprising (i) a source able to (a) emit a beam of therapeutic radiation along a beam axis and (b) rotate about a rotation axis that is substantially coincident with the beam axis, thereby to describe an arc around that axis, (ii) a multi-leaf collimator arranged to collimate the beam to a desired shape, and (iii) a control means able to control the dose rate of the source, the rotation of the source, and the multi-leaf collimator, the treatment planning apparatus being arranged to divide the arc into a plurality of arc-segments and to prepare a treatment plan which includes a first arc-segment adapted such that through the delivery of a certain number of mu first specified dose during which the source rotates a certain number of degrees first specified angle and the multi-leaf collimator changes shape at a first specified rate per degree, and similarly over a second arc segment adapted to deliver a second specified dose during which the source rotates a second specified angle and the multi-leaf collimator changes shape at a second specified rate per degree, such that at least one of the first and second specified doses, the first and second specified angles, and the first and second specified rates per degree, mu per degree rotation and the mu per mm MLC leaf movement are constant at a level different as between the first and second arc-segments.

It is preferred that the beam axis and the axis of rotation of the source are substantially orthogonal, for reasons of geometric simplicity.

As will be apparent from the above, we prefer that the rotation speed and the dose rate are both constant during an arc-segment, but that at least one thereof is different as between the first arc-segment and the second arc-segment.

Generally, we intend that the first arc-segment and the second arc-segment are consecutive. However, there may be specific instances where individual consecutive arc-segments do in fact have the same rotation speed and dose rate. However, in a treatment plan according to the present invention there will be pairs of arc segments for which at least one is different.

The treatment planning apparatus will of course include an output means of some form, for transmitting the treatment plan to the radiotherapeutic apparatus.

The treatment planning apparatus can further prescribe a treatment plan that includes motion of a patient positioning system during the treatment, in a manner correlated with motion of the source and/or delivery of the dose. This will (inter alia) allow HIMAT treatments to be provided.

BRIEF DESCRIPTION OF THE DRAWINGS

An embodiment of the present invention will now be described by way of example, with reference to the accompanying figures in which.

DETAILED DESCRIPTION OF THE EMBODIMENTS

A desired treatment is described by a Treatment Planning computer in terms of a sequence of "control points". Each "control point" defines a position of the gantry, the dose that is to be delivered between this and the next (or previous) control point, and the shape of the MLC at that control point. Each consecutive pair of control points defines (between them) an arc-segment.

Control points could (in theory) be spaced strategically around the complete arc. However, the availability of relatively cheap processing power means that there is little benefit in going to the effort of doing so, and control points are therefore typically spaced regularly around the arc such as every degree, every few degrees, or every fraction of a degree.

This treatment is put into effect by, between the $n^{th}$ and the $(n+1)^{th}$ control point, moving the gantry from the position of the $n^{th}$ control point to the position of the $(n+1)^{th}$ control point at a rotation speed and a dose rate that combine to deliver the required dose, while moving the MLC leaves at a substantially constant rate so that when the gantry is at the $(n+1)^{th}$ control point, the leaves are in the correct position for that point. This process is started at n=1, and then repeated for the arc-segment between the $(n+1)^{th}$ and the $(n+2)^{th}$ control points, and so on until the treatment is complete.

Figure 1:
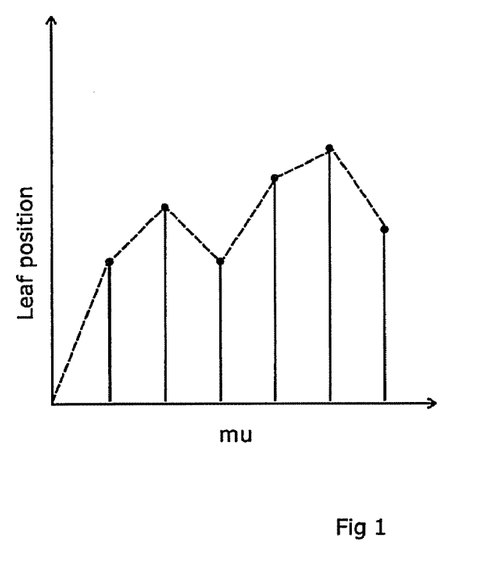
FIG. 1 is a graph showing the optimised control points from the Treatment Planning computer as to the leaf position and dose.
Figure 2:
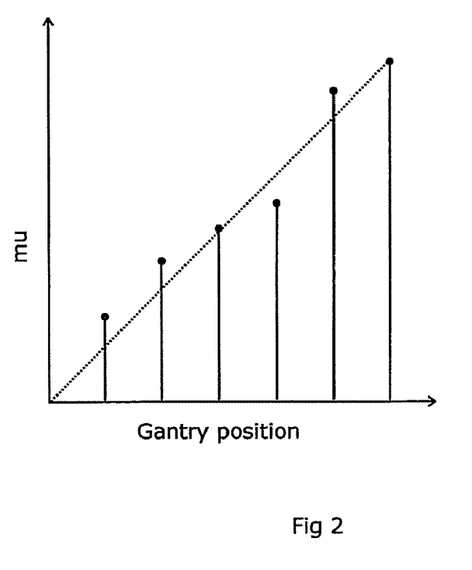
FIG. 2 is a graph showing the optimised control points from the Treatment Planning computer as to the gantry position and dose delivered as treatment progresses, and the approximation imposed by a constant mu per degree.

Thus, FIGS. 1 and 2 show a pattern of control points for a treatment. FIG. 1 shows graphically the details of the control points in terms of the position of a specific MLC leaf as the treatment progresses. During the treatment, tracked in terms of the total mu dose delivered so far, the leaf initially extends, retracts, and subsequently extends again. The dotted line shows the instantaneous position of the leaf, given that the control apparatus will move the leaf at a steady rate between control points so that by the time the next point is reached, the leaf is at the desired position. Similar graphs will exist for each of the (typically) 80 leaves; each graph will generally have more than 6 control points, such as 45, 90 or 180 control points.

FIG. 2 shows the details of the control points in terms of total dose delivered as the gantry rotates. Thus, the points are on a monotonically rising scale. However, the amount of the increase between successive control points varies, corresponding to some gantry angles at which more radiation is delivered and some at which less is delivered. The latter will generally correspond to angles at which the target structure is obscured by a critical structure. The variation in dose delivered can be achieved by variation of either the dose rate per time or the gantry rotation speed, or both. Clearly, a reduction in the cumulative dose delivered between a range of positions can be achieved by increasing the rotation speed or by reducing the dose rate. FIG. 2 shows in a dotted line the approximation that is imposed by requiring a constant mu per degree; this reduces the flexibility and either requires a less optimal dose distribution, or requires the variation to be taken up by way of the MLC positions thereby extending the treatment time.

Figure 3:
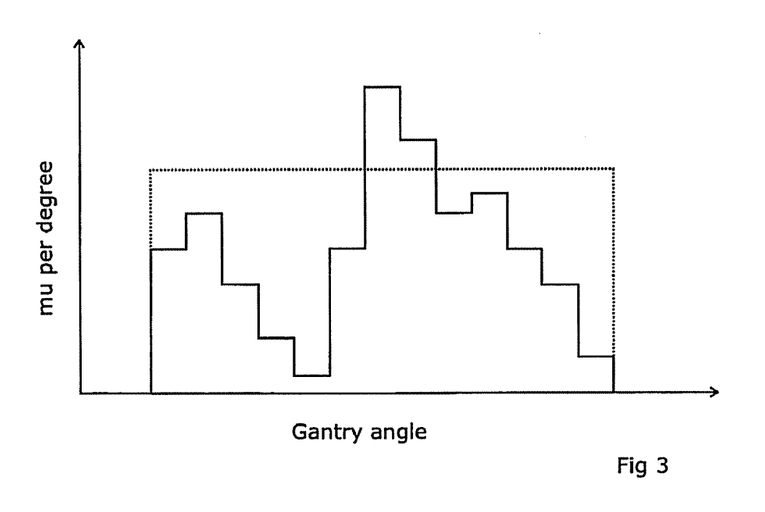
FIG. 3 shows the effect of the control points of FIG. 2, in terms of the dose rate, together with the same approximation.

FIG. 3, shows the result of FIG. 2, in terms of the dose rate at each gantry angle. At some gantry angles, the dose rate is high, indicating that a clear view of the target structure is available. At other gantry angles, the dose rate is markedly reduced indicating that the target may be obscured by a critical structure.

Thus, FIGS. 1 to 3 illustrate the treatment plan that is developed by the treatment planning computer, freed of the constraints imposed by previously known apparatus. It now remains for the treatment control computer of the radiotherapy apparatus to translate that treatment plan into a set of gantry moves, dose rates, and MLC moves.

Now, the minimum time in which each arc-segment can be delivered may be defined by the dose or the gantry or any one of the leaves in the MLC. Thus:

Minimum dose time=inter-control point dose/Maximum dose rate,

Minimum gantry time=Distance of gantry move/Maximum gantry speed,

Minimum leaf time=Distance of leaf move/Maximum leaf speed, (considered for each of the moving leaves)

The minimum time for the arc-segment is then the highest of all these minima. This defines the time limiting parameter, which may be the gantry, dose or any of the 80 leaves.

If the dose is not the time limiting parameter, then the desired dose rate can then be selected, being calculated as follows:

Desired dose rate=Control point dose/Minimum time

If the dose is the time limiting parameter, then the selected dose rate is of course the maximum dose rate.

The expected speeds of the Gantry and leaves can then be calculated from the selected dose rate as follows:

Expected arc-segment time=Control point dose/Selected dose rate

Expected gantry speed=Distance of gantry move/Expected arc-segment time and for each of the leaves in the MLC:

Expected leaf speed=Distance of leaf move/Expected arc-segment time

Figure 4:
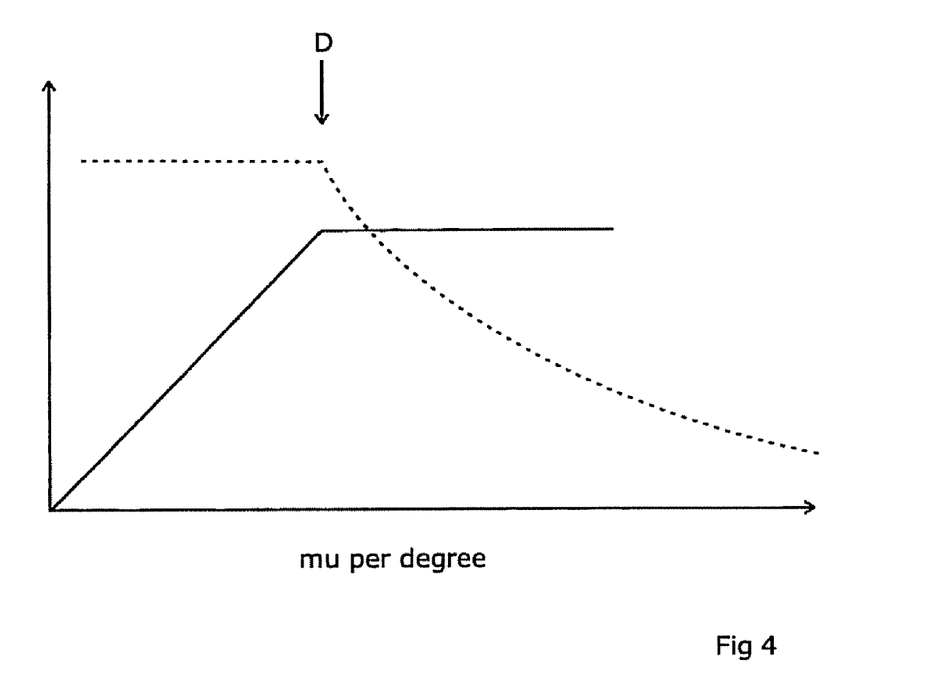
FIG. 4 shows an ideal calculation of the dose rate (solid line) and rotation speed (dashed line)

FIG. 4 shows the choice between the dose rate and the gantry speed, ignoring the influence of MLC leaf speed for the purposes of illustration. The x-axis is the dose rate per degree that is achieved, which corresponds to the cumulative dose delivered between two control points. The solid line is the dose rate, while the dotted line is the gantry rotation speed. Both have maximum rates imposed by the limitations of the specific apparatus being used. Thus, there is a specific dose D per unit rotation that is achieved by the apparatus operating at its maximum rotation speed and the maximum dose rate (per unit time).

To achieve a dose per unit rotation that is higher than D, the rotation speed must be decreased in inverse proportion, and the rotation speed (dotted line) in this region therefore shows a 1/x profile while the dose rate (solid line) is steady. To achieve a dose rate per unit rotation lower than D, the dose rate must be reduced proportionately as shown.

FIG. 4 therefore illustrates the above calculations in a graphical form.

It should be noted that some radiotherapeutic apparatus do not actually allow a continuously variable dose rate. Instead, the dose rate is only permitted to adopt one of a number of preset levels. In such a case, the highest available dose rate that is less than the desired dose rate should be selected. The other factors can then be determined as above.

Figure 5:
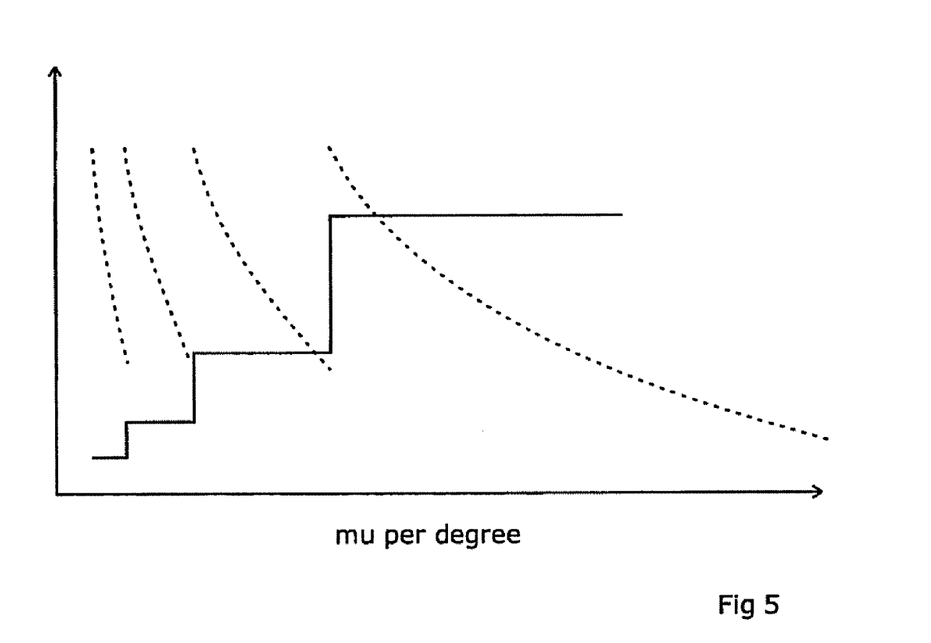
FIG. 5 shows an practical calculation of the dose rate (solid line) and rotation speed (dashed line) in a system without a continuously variable dose rate.

This is illustrated in FIG. 5. This corresponds to FIG. 4 except that in the region of FIG. 4 where the dose rate is linear, the dose rate is forced to increase in steps up to the maximum dose rate. This is compensated for by the rotation speed profile which adopts a series of 1/x curves for each step, instead of simply for the maximum dose rate. Thus, the use of an apparatus without a continuously variable dose rate per unit time incurs a penalty in terms of the treatment time required but not in terms of the dose distribution.

Ideally, the actual positions will be servoed to the actual delivered dose and therefore the actual speeds will vary slightly from the expected speeds. However, the expected speed is a very useful parameter to ensure that the servos perform optimally.

In this way, a system is produced that is sufficiently close to ERDMLC in practice to mean that it can be treated as an ERDMLC system for most purposes.

Figure 6:
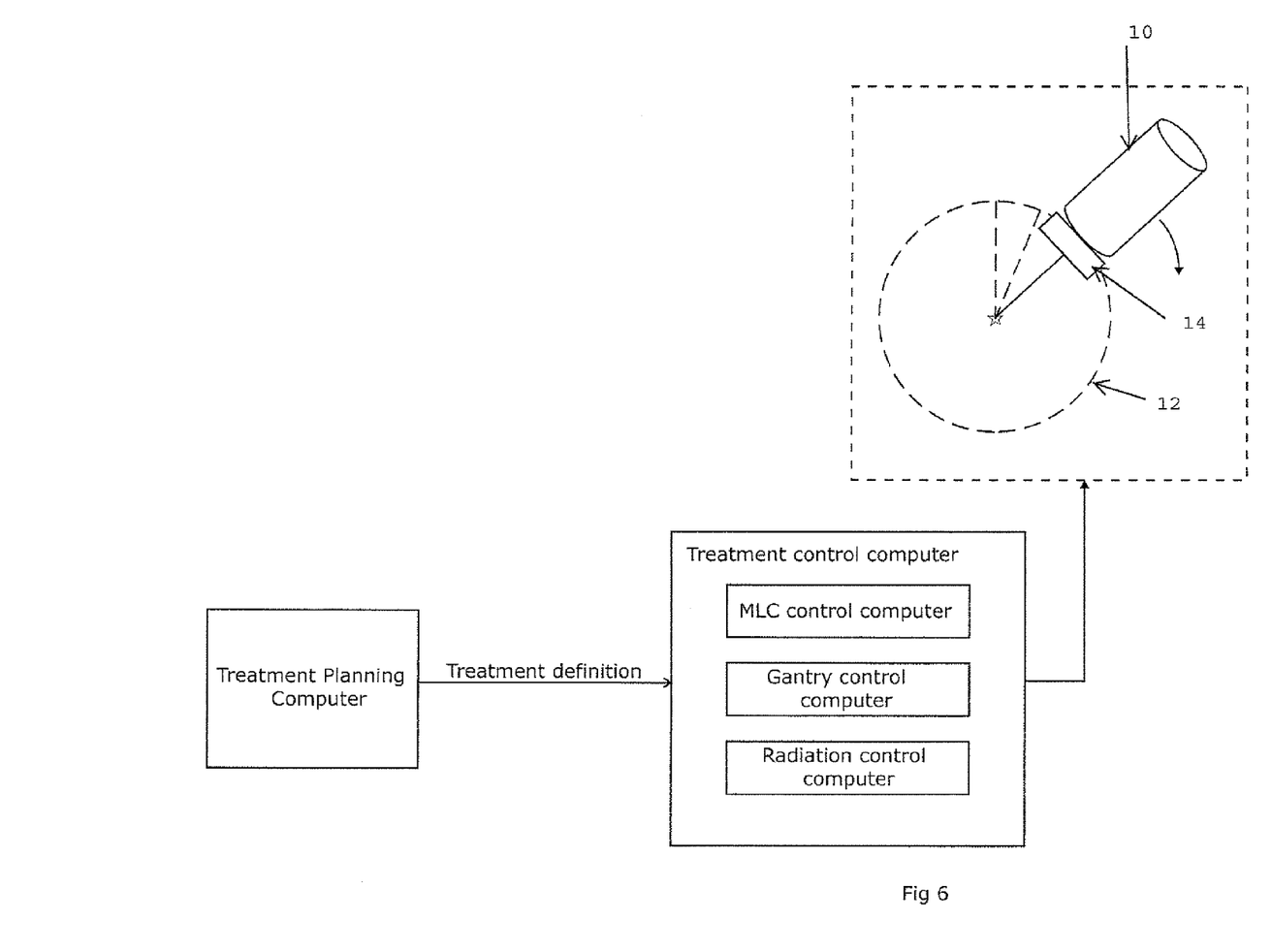
FIG. 6 shows the relationship between the computers.

FIG. 6 shows a radiotherapeutic or treatment planning apparatus demonstrating the relationships between the various computers involved in the system. Shown in the radiotherapeutic apparatus is a radiation source 10 able to emit a beam of therapeutic radiation along a beam axis and a MLC 14 arranged to collimate the beam to a desired shape. Radiation source 10 is shown to rotate about a rotation axis to define or describe an arc 12. A beam axis intersects with the rotation axis. As shown and described, the arc 12 is divided into a plurality of arc segments. The treatment planning computer develops a treatment plan which defines the treatment and passes this to a treatment control computer. This determines, for each arc-segment, which factor is the time-limiting factor and is thereby able to instruct each of the MLC control computer, gantry control computer, and radiation control computer as to the operation of their specific item during that arc-segment.

In practice, it will be necessary to decide whether each illustrated computer should exist as a separate entity or whether some or all should be combined into a single processor. This decision will depend on the pattern of expected computational load and the processing power available.

Such a treatment plan can be implemented on a radiotherapy machine that is substantially akin to those in current use. The physical differences called for by this invention lie in the control apparatus and the treatment planning apparatus; the actual radiation head and the means for driving it, its MLC and other systems can be as those in current use. However, there are certain changes to the apparatus that could be useful in the context of a machine operating in this manner.

First, the reeling system for the radiation head would benefit from being able to travel more than 360°, such as 2, 3 or more rotations. This would allow an operator to treat 3 or more IMAT arcs without stopping, and also to image and treat the patient in a continuous arc from underneath.

Second, we propose to enclose the whole machine in a set of covers similar in style to a CT or MR machine, with the bore preferably closed off at the inside end. Enclosing the moving parts removes the possibility of a hazardous collision and therefore enables the speed of the gantry to be increased fairly easily from 1 RPM to at least 2 or possibly up to 5 or 6, reducing the treatment times significantly. Increased speed also offers new options for Cone Beam image acquisition for example the images can be acquired during a single breath hold thereby eliminating any artefacts due to breathing motion.

Finally, to further reduce treatment times at high rotational speeds we propose to remove the flattening filters that are normally placed in the path of the beam in order to give a more uniform intensity of radiation across the aperture of the device. These filters do of course act by reducing the intensity of the beam in the central area of the aperture, and therefore the compromise is between uniformity and overall dose. A non-flat or non-uniform beam could instead be characterized and compensated for in treatment planning. This would avoid difficulties relating to the non-uniformity of the beam intensity since adjustments would be made in the other treatment parameters, and would allow a reduction in treatment time commensurate with the "recovery" of radiation that was otherwise removed by the flattening filter.

It will of course be understood that many variations may be made to the above-described embodiment without departing from the scope of the present invention.

The invention claimed is:

1. A radiotherapeutic apparatus comprising:
a source able to emit a beam of therapeutic radiation along a beam axis, wherein the source is rotatable about a rotation axis that is substantially orthogonal to and intersects with the beam axis thereby to describe an arc around the rotation axis;
a multi-leaf collimator arranged to collimate the beam to a desired shape; and
a control means able to control dose/time rate of the source, rotation speed of the source, and a position of the multi-leaf collimator,
the control means being arranged to receive a treatment plan in which the arc is divided into a plurality of arc-segments, the treatment plan specifying a total dose for an arc-segment and a start and end MLC position, and to control the source in accordance with the treatment plan over the arc-segment by calculating total time required for the arc-segment for a plurality of factors including:
   i. an MLC leaf movement from a prescribed position at the start of the arc-segment to a prescribed position at the end of the arc-segment, at a maximum leaf speed;
   ii. rotation of the source from the start to the end of the arc-segment at a maximum source rotation speed;
   iii. delivery of the dose at a maximum dose rate per time;
the control means being arranged to select a factor dictating a longest time, and control the apparatus so that the selected factor operates at its respective maximum and remaining factors are operated at a reduced rate selected to match the longest time.

2. The radiotherapeutic apparatus according to claim 1 wherein the control means comprises a treatment control computer and an actuator.

3. The radiotherapeutic apparatus according to claim 1 in which the radiation is not interrupted between the first arc-segment and the second arc-segment.

4. The radiotherapeutic apparatus according to claim 1 arranged to monitor the dose actually delivered during a treatment and an actual position of the source, compare this to the treatment plan, and servo the position of the source and or the dose rate so that the actual relationship between delivered dose and source position corresponds substantially to the treatment plan.

5. The radiotherapeutic apparatus according to claim 1 arranged to monitor the dose actually delivered during a treatment and the actual position of the MLC, compare this to the treatment plan, and servo the position of the MLC and or the dose rate so that the actual relationship between delivered dose and MLC position corresponds substantially to the treatment plan.

6. The radiotherapeutic apparatus according to claim 1 arranged to monitor the dose actually delivered during a treatment and the actual position of the patient positioning system, compare this to the treatment plan, and servo the position of the patient positioning system and or the dose rate so that the actual relationship between delivered dose and patient positioning system position corresponds substantially to the treatment plan.

7. A treatment planning apparatus, for a radiotherapeutic apparatus of the type comprising (i) a source able to (a) emit a beam of therapeutic radiation along a beam axis and (b) rotate about a rotation axis that with the beam axis thereby to describe an arc around the rotation axis, (ii) a multi-leaf collimator arranged to collimate the beam to a desired shape, and (iii) a control means able to control dose rate of the source, rotation of the source, and the multi-leaf collimator;
the treatment planning apparatus being arranged to divide the arc into a plurality of arc-segments and to prepare a treatment plan which includes a first arc-segment adapted to deliver a first specified dose during which the source rotates a first specified angle and the multi-leaf collimator changes shape at a first specified rate per degree, and a second arc segment adapted to deliver a second specified dose during which the source rotates a second specified angle and the multi-leaf collimator changes shape at a second specified rate per degree, such that at least the first and second specified rates per degree differ as between the first and second arc-segments.

8. The treatment planning apparatus according to claim 7 in which the rotation speed and the dose rate are both constant during an arc-segment, and at least one thereof is different as between the first arc-segment and the second arc-segment.

9. The treatment planning apparatus according to claim 7 in which the first arc-segment and the second arc-segment are consecutive.

10. The treatment planning apparatus according to claim 7, further comprising an output means for transmitting the treatment plan to the radiotherapeutic apparatus.

11. The treatment planning apparatus according to claim 7 arranged to calculate an irradiation time for each arc-segment apt to deliver a required dose and to infer a rotation speed from the irradiation time.

12. The treatment planning apparatus according to claim 7 arranged to prescribe a treatment plan that includes motion of a patient positioning system during the treatment in a manner correlated with motion of the source.

13. The treatment planning apparatus according to claim 7 arranged to prescribe a treatment plan that includes motion of a patient positioning system during the treatment in a manner correlated with delivery of the dose.

14. The treatment planning apparatus according to claim 7 in which the beam axis and the axis of rotation of the source are substantially orthogonal.

* * * * *

UNITED STATES PATENT AND TRADEMARK OFFICE
CERTIFICATE OF CORRECTION

| | |
|---|---|
| PATENT NO. | : 7,961,843 B2 |
| APPLICATION NO. | : 12/297891 |
| DATED | : June 14, 2011 |
| INVENTOR(S) | : Kevin Brown et al. |

It is certified that error appears in the above-identified patent and that said Letters Patent is hereby corrected as shown below:

<u>Claim 7</u>

Column 10, line 19, after "that", insert --intersects--.

Signed and Sealed this
Tenth Day of July, 2012

David J. Kappos
*Director of the United States Patent and Trademark Office*